(12) United States Patent
Chang

(10) Patent No.: US 7,892,023 B2
(45) Date of Patent: Feb. 22, 2011

(54) CONNECTOR CAPABLE OF READING IMAGE

(76) Inventor: Nai-Chien Chang, 5F., No. 15, Lane 117, Sec. 4, Sanhe Rd., Sanchong City, Taipei County 241 (TW)

( * ) Notice: Subject to any disclaimer, the term of this patent is extended or adjusted under 35 U.S.C. 154(b) by 0 days.

(21) Appl. No.: 12/619,775

(22) Filed: Nov. 17, 2009

(65) Prior Publication Data

US 2010/0203764 A1  Aug. 12, 2010

(30) Foreign Application Priority Data

Feb. 12, 2009   (TW) ............................... 98202023 U

(51) Int. Cl.
*H01R 33/945* (2006.01)
(52) U.S. Cl. ..................................... 439/577
(58) Field of Classification Search ................ 439/577, 439/607.24, 490, 620.16, 620.17, 620.18, 439/620.19
See application file for complete search history.

(56) References Cited

U.S. PATENT DOCUMENTS

| | | | |
|---|---|---|---|
| 7,192,198 B1 * | 3/2007 | Chen et al. ................... 385/76 |
| 7,534,140 B2 * | 5/2009 | Zheng et al. ............ 439/607.01 |
| 2005/0157459 A1 * | 7/2005 | Yin et al. ..................... 361/683 |
| 2006/0036784 A1 * | 2/2006 | Loo ............................. 710/62 |
| 2006/0234554 A1 * | 10/2006 | Tsai ............................ 439/607 |

* cited by examiner

*Primary Examiner*—Phuong K Dinh
(74) *Attorney, Agent, or Firm*—Chun-Ming Shih; HDLS IPR Services

(57) ABSTRACT

A connector capable of reading image includes an outer shell, a seat body, a rear lid body and an image-reading module. The outer shell has a front decorative plate, two sides of which are extended two lateral plates corresponding to each other, and an upper edge of which has a folded plate folded between the two lateral plates, and which has a plurality of perforations arranged thereon. The seat body is disposed in the outer shell and has a first interface and a second interface, both of which are arranged at a front face of the seat body and corresponded to the plural perforations. An electric connector is disposed in the second interface. The rear lid body is disposed at a rear side of the seat body. The image-reading module, which is disposed in the first interface, is comprised of a circuit board, a camera, a signal-converting unit and a plurality of electrically conductive terminals. After the camera reads the external image, the analogous signals are converted into digital signals by a signal-converting unit. Then, the digital signals are output via the plural thermally conductive terminals.

9 Claims, 5 Drawing Sheets

CONNECTOR CAPABLE OF READING IMAGE

BACKGROUND OF THE INVENTION

1. Field of the Invention

The present invention in general relates to a connector, in particular, to a connector capable of reading image.

2. Description of Prior Art

Accordingly, "electric connector" here means the connection component or the accessory adapted in all electronic signal and power source. For example, the peripherals of a computer, such as mouse, display, keyboard, printer, etc. all need connectors to connect them to one another. Or, in a facility, there are connectors needed to connect the appliance signals among each modules, for example, IC socket, board edge connector, etc., all of which need connector as well. Therefore, in terms of electronic products, electric connector is one of the most important components.

Recently, technology has being developed continuously, so a lot of electric connectors of new generation have been manufactured, for example, USB, HDMI, Displayport, eSATA, SATA. In these electric connectors, some can simplify the multiple transmission cables and boost the transmission speed. For example, in the past, when intending to transmit sound and image, at least three transmission cables are needed, but now, only one HDMI then can achieve the transmission of sound and image. Or, the connectors constituted by multiple functions can be stacked up or connected together to form a kind of multi-ported connector, a single one of which can be plugged in by multiple transmission cables of a variety of functions. However, the aforementioned connectors are only adapted for simplifying the winding of multiple cables at outside of an electronic product and solving the problems of data transmission speed and adaptation of multiple transmission cables to be plugged in.

In addition, because of population and trend, some electric devices are additionally arranged cameras capable of reading image. However, there are few users, who really need the function of camera or can afford time to use it. It is unnecessary for a user to pay more in purchasing an electric device having an extra camera, which is not really wanted.

Accordingly, after a substantially devoted study, in cooperation with the application of relative academic principles, the inventor has finally proposed the present invention designed reasonably to possess the capability to improve the drawbacks of the prior arts significantly.

SUMMARY OF THE INVENTION

Therefore, in order to solve aforementioned problems, the invention is mainly to provide a connector capable of reading image, which is arranged a camera therein. When a user needs to read the image signals, the connector having camera can be installed onto an electric device.

Secondly, the invention is to provide a connector capable of reading image, electrically connected to an electronic device, including:

an outer shell, on which has a front decorative plate, two sides of which are extended two lateral plates corresponding to each other, and an upper edge of which has a folded plate folded between the two lateral plates, and which has a plurality of perforations arranged thereon;

a seat body, which is disposed in the outer shell and has a first interface and a second interface, both of which are arranged at a front face of the seat body and corresponded to the plural perforations; in the meantime, an electric connector is disposed in the second interface;

a rear lid body, which is disposed at a rear side of the seat body; and an image-reading module, which is disposed in the first interface, and which is comprised of a circuit board, a camera, a signal-converting unit and a plurality of electrically conductive terminals; after the camera reads the external image, the analogous signals is converted into digital signals by a signal-converting unit, then the digital signals is output to the electric device via the plural thermally conductive terminals.

BRIEF DESCRIPTION OF DRAWING

The features of the invention believed to be novel are set forth with particularity in the appended claims. The invention itself, however, may be best understood by reference to the following detailed description, which describes an embodiment of the invention, taken in conjunction with the accompanying drawings, in which:

DETAILED DESCRIPTION OF THE INVENTION

In cooperation with attached drawings, the technical contents and detailed description of the present invention are described thereinafter according to an preferable embodiment, not used to limit its executing scope. Any equivalent variation and modification made according to appended claims is all covered by the claims claimed by the present invention.

Figure 1:
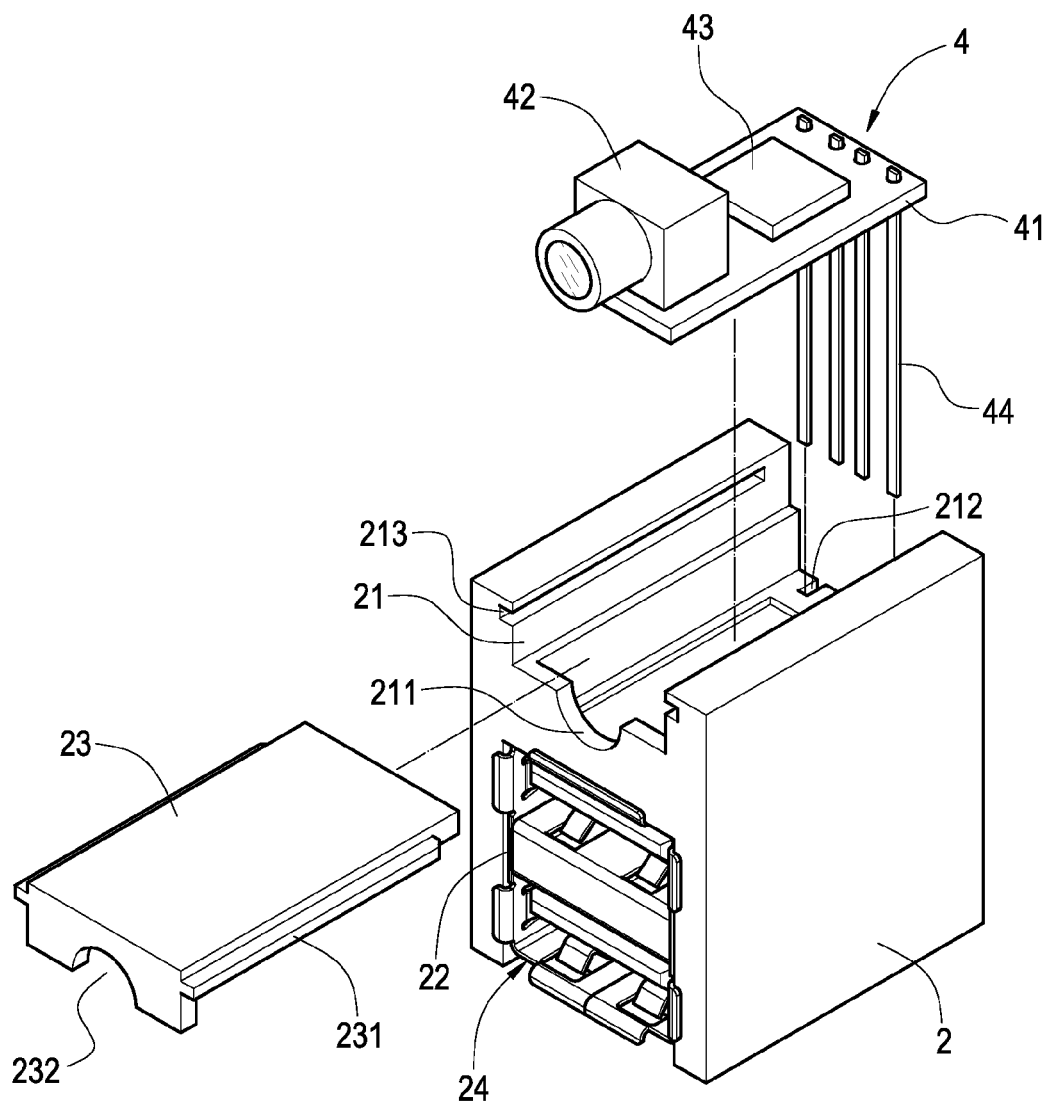
FIG. 1 is an explosive illustration of a seat body according to the present invention.
Figure 2:
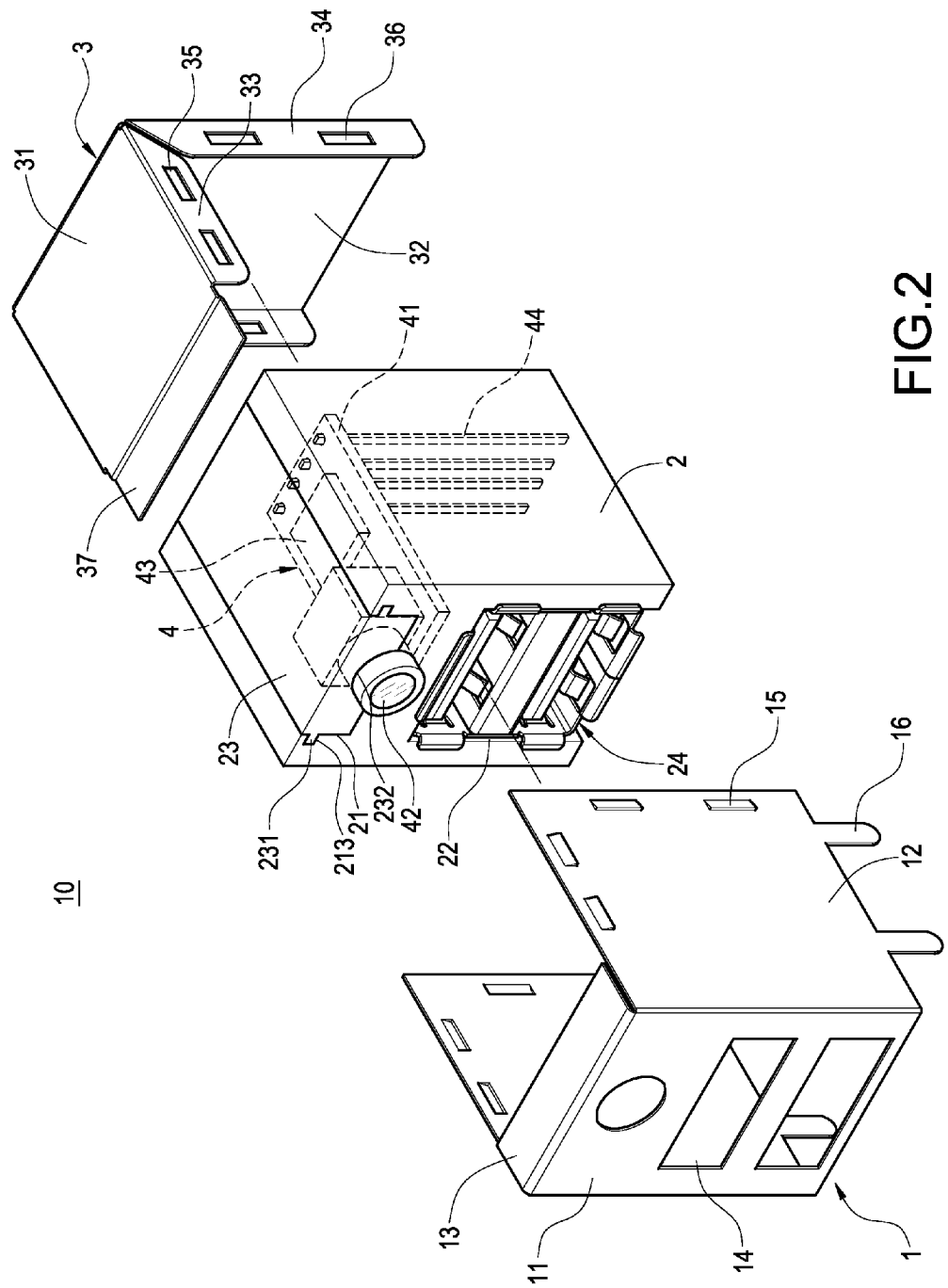
FIG. 2 is an explosive illustration of a connector according to the present invention.
Figure 3:
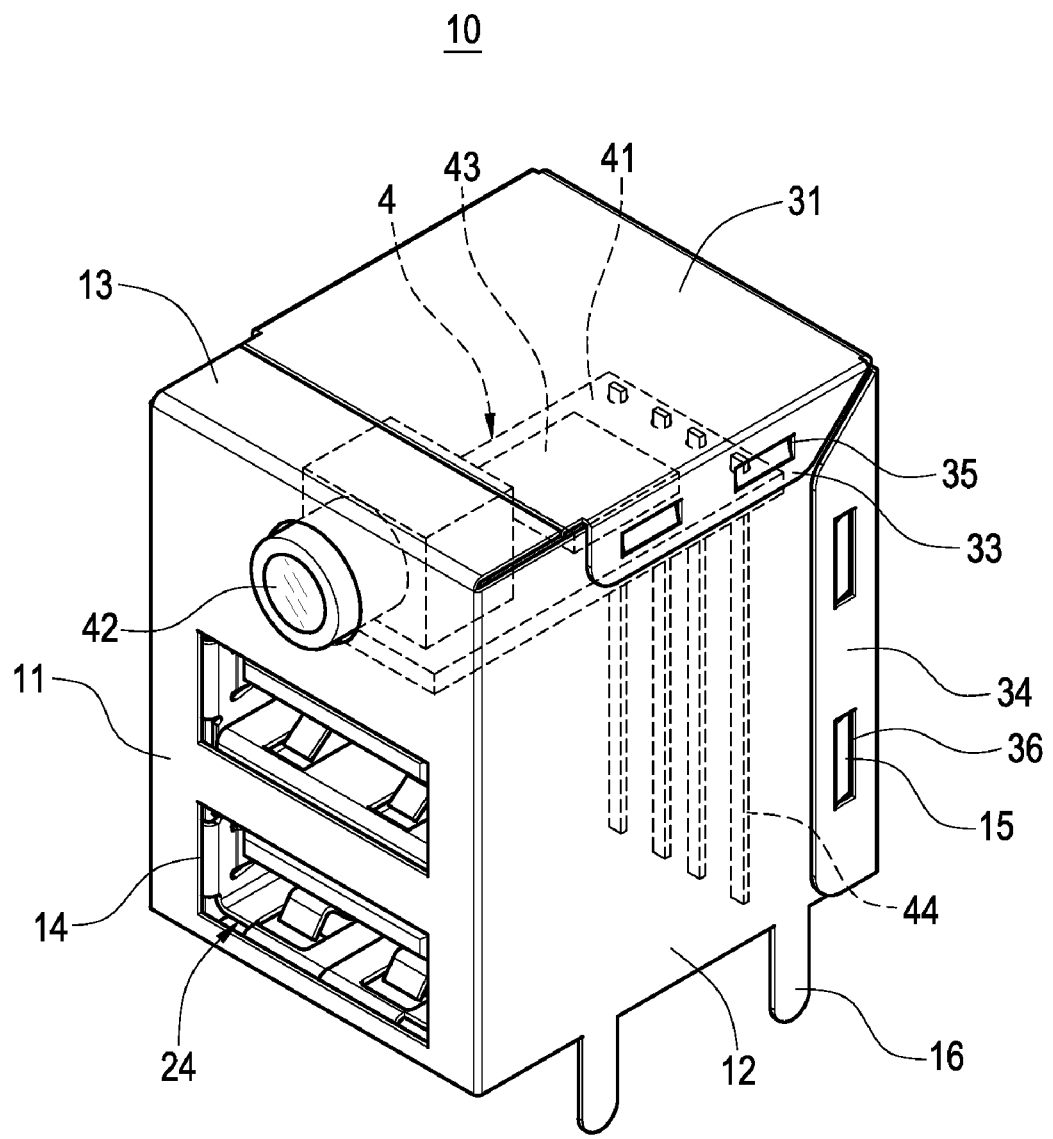
FIG. 3 is an assembled illustration of a connector according to the present invention.

Please refer to FIG. 1, FIG. 2 and FIG. 3, which separately are an explosive illustration of a seat body, an explosive illustration of a connector, and an assembled illustration according to the present invention. As shown in these figures: a connector 10 according to the present invention includes an outer shell 1, a seat body 2, a rear lid body 3 and an image-reading module 4.

The outer shell 1 is made of a metallic material and formed as a "U"-shape configuration, on which has a front decorative plate 11, two sides of which are extended two lateral plates 12 corresponding to each other, and an upper edge of which has a folded plated folded between the two lateral plates 12, and on which there are a plurality of perforations 14. In addition, a plurality of jointing convex blocks 15 are arranged on the lateral plates 12, and a plurality of connection legs 16 are extended from lower edges of the lateral plates 12 and adapted for connecting fixedly to a motherboard of an electronic device (not shown in the figures).

The seat body 2 is disposed in the outer shell 1 and has a first interface 21, a second interface 22, a slip lid 23 and an electric connector 24 arranged thereon. A front side of the first interface 21 has a semi-circular opening 211 and a rear side thereof has a plurality of grooves 212. A pair of slip troughs 213 corresponding to each other are arranged on two lateral walls in the seat body 2. After two slides 231 convexly arranged at two lateral sides of the slip lid 23 is slipped into the lip troughs 213, the slip lid 23 is assembled above the first interface 21. In the meantime, a front side of the slip lid 23 has a semi-circular opening 232. When the image-reading module 4 is disposed in the first interface 21, the camera 42 is sandwiched between the openings 211, 232 in the front of the first interface 21, letting the camera 42 shown as an exposure status. Furthermore, an electric connector 24 is disposed in the second interface 22. The electric connector 24 is any kind of USB, HDMI, Displayport, PS/2, eSATA, micro-USB, MINI USB, and IEEE1394 and can be stacked up or aligned up to form a kind of multi-ported connector.

The rear lid body 3 has a top plate 31 and a rear plate 32 arranged thereon, two sides of each of which have two jointing parts 33, 34 arranged symmetrically, on which a plurality of jointing holes 35, 36 are arranged to be jointed with the plural jointing convex blocks 15. In the meantime, a front side of the top plate 31 has a tongue 37 capable of being inserted into the folded plate 13. After the lid body 3 is assembled into the outer shell 3, the seat body 2 is enclosed to form a metallic mast capable of preventing any interference generated from electromagnetic waves.

The image-reading module 4, which is disposed in the first interface 21, is comprised of a circuit board 41, a camera 42, a signal-converting unit 43 and a plurality of electrically conductive terminals 44. The plural electrically conductive terminals 44 are disposed in the plural grooves 212. The camera 42, the signal-converting unit 43 and the plural electrically conductive terminals 44 are electrically connected to the circuit board 41. After the camera 42 reads the outside image, the image signal is transmitted to the signal-converting unit 43 via the circuit board 41. The signal-converting unit 43 then converts the analogous signal into the digital signal. Then, the digital signal is in turn transmitted to the electronic device (not shown in the figures) via the plural electrically conductive terminals 44. In this preferable embodiment, the signal-converting unit 43 is an analogous/digital converter.

Figure 4:
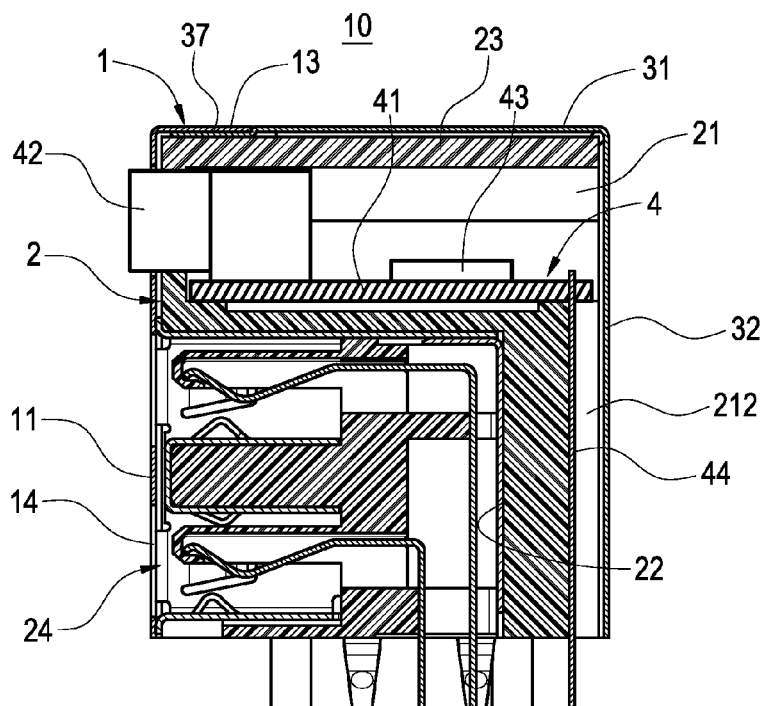
FIG. 4 is a cross-sectional illustration of a connector according to the present invention.

Please refer to FIG. 3 and FIG. 4, which respectively show an assembled and cross-sectional illustration of a connector according to the present invention. As shown in these figures: after the connector 10 and the image-reading module 4 are assembled, the image-reading module 4 of the first interface 21 can be adapted for a user to read the outside image data, while the electric connector 24 of the second interface 22 can be adapted for the USB transmission cable to be plugged therein, thereby, a transmission of data being undergoing. In this embodiment, for the purpose of description, a USB connector is taken as an example of the electric connector 24. However, in the scope of the invention, the electric connector 24 is not limited to the USB connector only.

Figure 5:
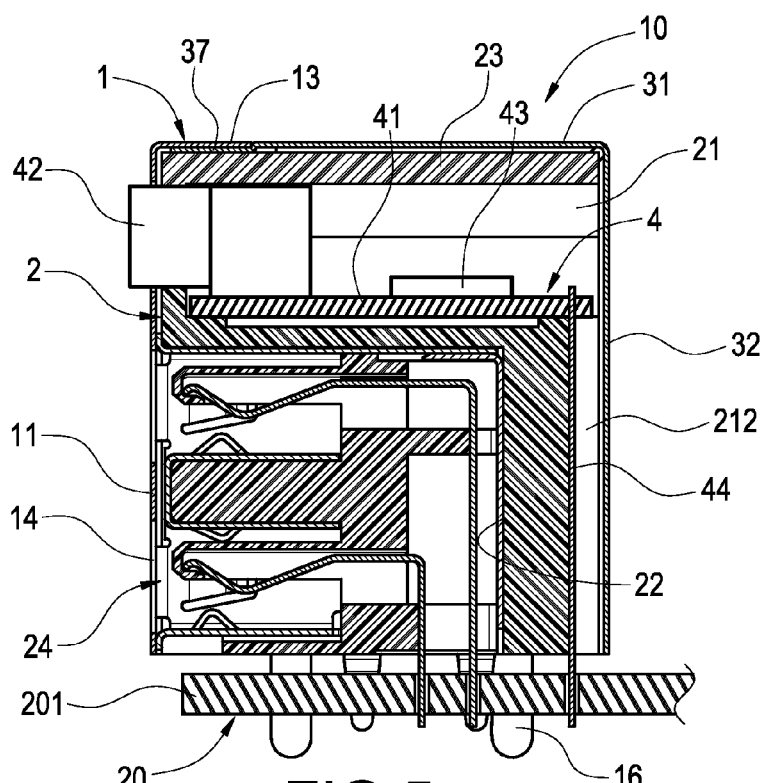
FIG. 5 is a cross-sectional illustration of a connector according to the present invention electrically connected to an electronic device.
Figure 6:
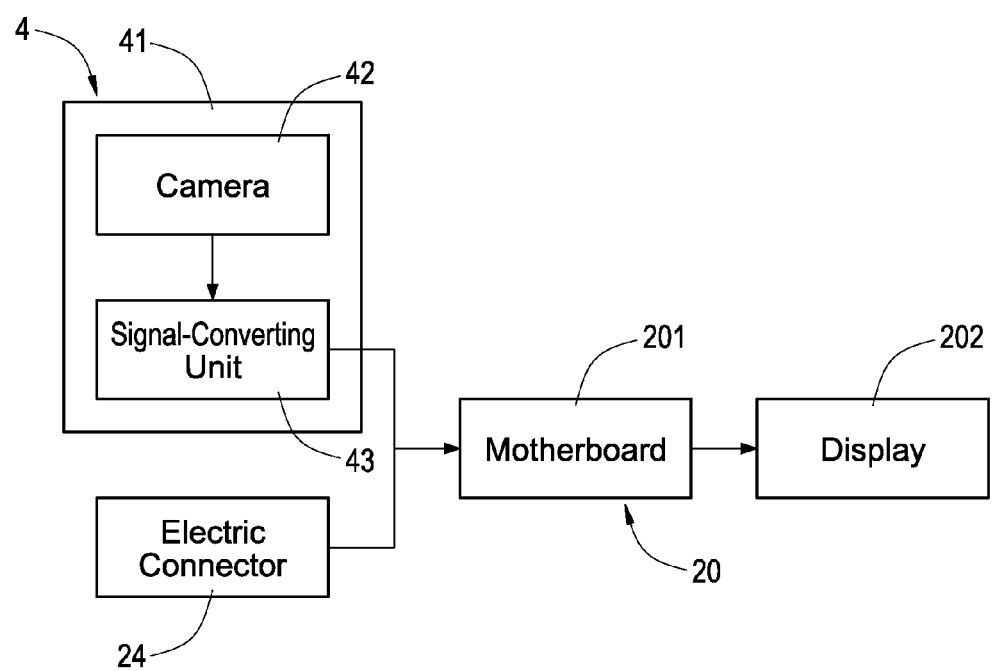
FIG. 6 is a circuit block illustration of a connector according to the present invention electrically connected to an electronic device.

Please refer to FIG. 5 and FIG. 6, which respectively show a cross-sectional and circuit block illustration of a connector according to the present invention electrically connected to an electronic device. As shown in these figures: after the connector 10 of the invention is electrically connected to a motherboard 201 of the electronic device 20, the camera 42 controlled by the circuit of the motherboard 201 can read the outside image to generate an analogous signal. Afterwards, the image signal is transmitted to the signal-converting unit 43, where the analogous signal is converts into a digital signal for outputting to a motherboard 201 of the electronic device 20 via the plural electrically conductive terminals 44. After processed by the circuit on the motherboard 201, the read image signal is then displayed on a display 202.

Therefore, after the connector 10 capable of reading outside image signal is matched up for use with the electronic device, all the electronic device originally without the function of reading image can possess the function of reading image signal now.

Therefore, through the constitution of aforementioned assemblies, a connector capable of reading image according to the present invention is thus obtained.

Summarizing aforementioned description, the connector capable of reading image according to the present invention is an indispensable component for an electric device indeed, which may positively reach the expected usage objective for solving the drawbacks of the prior arts, and which extremely possesses the innovation and progressiveness to completely fulfill the applying merits of a new type patent, according to which the invention is thereby applied. Please examine the application carefully and grant it as a formal patent for protecting the rights of the inventor.

However, the aforementioned description is only a preferable embodiment according to the present invention, not used to limit the patent scope of the invention, so equivalently structural variation made to the contents of the present invention, for example, description and drawings, is all covered by the claims claimed thereinafter.

What is claimed is:

1. A connector, capable of reading image, electrically connected to an electronic device, including:
    an outer shell, on which has a front decorative plate, two sides of which are extended two lateral plates corresponding to each other, and an upper edge of which has a folded plate folded between the two lateral plates, and which has a plurality of perforations arranged thereon;
    a seat body, which is disposed in the outer shell and has a first interface and a second interface, both of which are arranged at a front face of the seat body and corresponded to the plural perforations, in the meantime, an electric connector being disposed in the second interface;
    a rear lid body, which is disposed at a rear side of the seat body; and
    an image-reading module, which is disposed in the first interface and is comprised of a circuit board, a camera, a signal-converting unit and a plurality of electrically conductive terminals, wherein the camera, the signal-converting unit and the plural electrically conductive terminals are electrically connected to the circuit board, and wherein the plural electrically conductive terminals are disposed in a plurality of grooves of the first interface and wherein, when the image-reading module is disposed to the first interface, the camera is placed under a slip lid and sandwiched between a first semi-circular opening of the slip lid and a second semi-circular opening of the first interface at the front of the first interface.

2. The connector according to claim 1, wherein the outer shell is made of a metallic material and formed as a "U"-shape configuration.

3. The connector according to claim 2, wherein a plurality of jointing convex blocks are arranged on the lateral plates of the outer shell, and wherein a plurality of jointing legs are extended from lower edges of the lateral plates.

4. The connector according to claim 3, wherein the rear lid body has a top plate and a rear plate, two sides of each of which have two jointing parts arranged symmetrically, on which a plurality of jointing holes are arranged to be jointed with the plural jointing convex blocks, and wherein a front side of the top plate has a tongue capable of being inserted into the folded plate.

5. The connector according to claim 1, wherein a front side of the first interface has the second semi-circular opening and a rear side thereof has a the grooves, and wherein a pair of slip troughs corresponding to each other are arranged on two lateral walls in the seat body.

6. The connector according to claim 5, wherein two sides of the slip lid are respectively arranged a slide, the two slides are slipped into the slip troughs, such that the slip lid is assembled above the first interface, and wherein a front side of the slip lid has the first semi-circular opening corresponding to the second semi-circular opening arranged in the front side of the first interface.

7. The connector according to claim 1, wherein the signal-converting unit is an analogous/digital converter.

8. The connector according to claim 1, wherein the electric connector is any kind of USB, HDMI, Displayport, PS/2, eSATA, micro-USB, MINI USB, and IEEE1394.

9. The connector according to claim 8, wherein the electric connectors can be stacked up or aligned up to form a kind of multi-ported connector.

* * * * *